United States Patent
Conti

(10) Patent No.: US 7,402,807 B2
(45) Date of Patent: Jul. 22, 2008

(54) METHOD FOR REDUCING AN ELECTRONIC TIME COINCIDENCE WINDOW IN POSITRON EMISSION TOMOGRAPHY

(75) Inventor: Maurizio Conti, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 404 days.

(21) Appl. No.: 11/265,758

(22) Filed: Nov. 2, 2005

(65) Prior Publication Data

US 2007/0106154 A1 May 10, 2007

(51) Int. Cl.
*G01T 1/164* (2006.01)
(52) U.S. Cl. .................................. 250/363.03
(58) Field of Classification Search ............. 250/363.03
See application file for complete search history.

(56) References Cited

U.S. PATENT DOCUMENTS

| | | | | |
|---|---|---|---|---|
| 2004/0195512 A1* | 10/2004 | Crosetto | ................. | 250/363.04 |
| 2005/0067571 A1* | 3/2005 | Yanagita et al. | ........ | 250/363.03 |
| 2006/0065825 A1* | 3/2006 | Ishitsu et al. | ............. | 250/252.1 |
| 2006/0074292 A1* | 4/2006 | Thomson et al. | ............ | 600/411 |
| 2006/0178575 A1* | 8/2006 | Piacsek et al. | .............. | 600/413 |
| 2006/0197025 A1* | 9/2006 | Burr et al. | .................... | 250/366 |
| 2007/0010731 A1* | 1/2007 | Mistretta | .................... | 600/407 |
| 2007/0167749 A1* | 7/2007 | Yarnall et al. | ............... | 600/431 |

* cited by examiner

*Primary Examiner*—David P. Porta
*Assistant Examiner*—Carolyn Igyarto

(57) ABSTRACT

A method for acquiring PET images with reduced time coincidence window limits includes obtaining a preliminary image of a patient within a radiation field of view (FOV), determining the spatial location of the patient within the FOV based on the preliminary image, calculating a different time coincidence window based on the spatial location of the patient for each possible pair of oppositely disposed detectors, scanning the patient with a PET scanning system to detect a pair of gamma photons produced by an annihilation event, determining whether the detection of the pair of gamma photons occurs within the time coincidence window, accepting the detected event only if the detection of the gamma photons occurs within the time coincidence window, calculating the spatial location of accepted annihilation event, and adding the calculated spatial location of the annihilation event to a stored distribution of calculated annihilation event spatial locations representing the distribution of radioactivity in the patient.

14 Claims, 4 Drawing Sheets

METHOD FOR REDUCING AN ELECTRONIC TIME COINCIDENCE WINDOW IN POSITRON EMISSION TOMOGRAPHY

FIELD OF THE INVENTION

The present invention generally relates to nuclear medicine, and systems for obtaining nuclear medicine images. In particular, the present invention relates to systems and methods for obtaining nuclear medicine images by detecting true coincident events resulting from positron annihilation.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce three-dimensional images for diagnosing the biochemistry or physiology in a specific organ, tumor or other metabolically active site. In PET events are detected from the decay or annihilation of positrons and electrons. When a positron is annihilated by an electron, two 511 keV gamma photons are simultaneously produced and travel in approximately opposite directions. Gamma photons produced by an annihilation event can be detected by a pair of oppositely disposed scintillating detectors capable of producing a signal in response to the interaction of the gamma photons with a crystal of the scintillating detectors. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence, they also identify a line of response, or LOR, along which the annihilation event has occurred. An example of a PET method and apparatus is described in U.S. Pat. No. 6,858,847, which patent is incorporated herein by reference in its entirety.

The number of time coincidences detected within a field of view (FOV) of a detector is the count rate of the detector. The count rate at each of two oppositely disposed detectors, A and B, can be referred to as singles counts, or singles, $S_A$ and $S_B$. The time required for a gamma photon to travel from its point of origin to a point of detection can be referred to as the time of flight, or TOF, of the gamma photon. TOF is dependent upon the speed of light c and the distance traveled.

A time coincidence, or coincidence event, is identified if the time difference between the arrival of signals in a pair of oppositely disposed detectors is less than a time coincidence window $\tau$. The number of coincidence events per second registered is commonly referred to as prompt coincidences P, or prompts. Prompt coincidences P include true coincidences T, or trues and random coincidences R, or randoms. True coincidences T are those physically correlated time coincidences, i.e., two gamma photons emitted in the process of annihilation or photons produced from the two primary gamma photons. Random coincidences R are those time coincidences that are not correlated, but randomly occur within $\tau$. The randoms from a pair of detectors are usually proportional to the time coincidence window $\tau$ according to the following formula: $R=\tau \cdot S_A \cdot S_B$.

In the case of a system composed of a plurality of detectors, the total randoms can be estimated as $R=k \cdot \tau \cdot S^2$, where S is the average single count rate per detector and k is a proportionality constant. The prompt coincidences P, which are used to reconstruct an image of the distribution of activity in the patient, are therefore the sum of true and random coincidences, (P=T+R). The presence and detection of randoms is problematic as they degrade the quality of the image and limit the rate of true data throughput. Consequently, given data transmission limits, the rejection of randoms at their origin increases the count rate capabilities for true coincidences. The primary method for reducing the number, or fraction, of randoms in the data stream has been to reduce the time coincidence window $\tau$. However, two factors have limited the reduction of the time coincidence window $\tau$; the time resolution of the system and the size of the field of view (FOV). While the time resolution of PET systems is consistently improving as a result of improvements in detector technology and electronics, the time coincidence window $\tau$ is generally limited by the size of the FOV, i.e. the time window $\tau$ must be large enough to accept coincidence photons from anywhere in the FOV, as explained in the following.

As illustrated in FIG. 1, if an annihilation event occurs at the center of a FOV, the TOF of the gamma photon detected in detector A ($T_A$) is equal to the time of flight of the gamma photon detected in detector B ($T_B$). If an annihilation event occurs at a distance $\Delta x$ from the center of the FOV, the difference between $T_A$ and $T_B$ is $\Delta t=2\Delta x/c$, where c is the speed of light. If r is the radius of the FOV, the TOF difference $\Delta t$ could take any value from $-2r/c$ to $+2r/c$, depending on the location of the event. Because a source, or location, of an annihilation event is unknown, a priori, the time coincidence window $\tau$ must be great enough to accept all true coincidence events occurring within the FOV, so $\tau$ must be greater than $4r/c$. The number of randoms that a conventional PET system can reject is, thus, limited by the required size of the time coincidence window $\tau$.

What is needed then is a method for performing PET such that randoms may be rejected beyond the above described time coincidence window limits.

SUMMARY OF THE INVENTION

The present invention addresses the above identified deficiencies by providing a method for reducing time coincidence window limits and thereby reducing random coincidences.

A method according to one embodiment of the invention broadly comprises obtaining a preliminary image of a patient within the field of view of a PET scanning system, describing the spatial location of the patient within the field of view, computing a time coincidence window for each pair of oppositely disposed detectors based on the spatial location of the contour of the patient and the probable intersection of such contour with the line connecting the detectors, scanning the patient with a PET scanning system to detect pairs of gamma photons produced by annihilation events, determining whether the detection of the pair of gamma photons occurs within the calculated time coincidence window, accepting and storing the event only if the detection of the gamma photons occurs within the time coincidence window, and processing the event in order to compute the location of the annihilation event and reconstruct the image of the original radioactivity distribution in the patient.

In an embodiment of the invention, a time coincidence window for a pair of oppositely disposed detectors can be described by the equation, $\tau_{low}(i,j)<(T_i-T_j)<\tau_{high}(i,j)$, wherein $(T_i-T_j)$ is the time of flight difference between the detection of a pair of gamma photons resulting from an annihilation event propagated along a line of response $LOR_{ij}$ between oppositely disposed detectors i and j, $\tau_{low}(i,j)$, which is also equal to $-2X_{ij\alpha}/c$, is a lower limit for time of flight difference between detectors i and j, $\tau_{high}(i,j)$, which is also equal to $2X_{ij\beta}/c$, is an upper limit for time of flight difference between detectors i and j, $X_{ij\alpha}$ is the distance from the center of the segment connecting the two detectors and the point $\alpha$, $X_{ij\beta}$ is the distance from the center of the segment connecting the two detectors and the point $\beta$, $\alpha$ and $\beta$ are the intersections of the contour of the patient and the said segment, and c is the speed of light.

In embodiments of the invention, the spatial location of a patient within the field of view can be described using Cartesian or polar coordinate axes systems, although other systems for describing the spatial location of a patient within the field of view can be utilized.

In an embodiment of the invention the preliminary image is obtained using the instrumentation typically associated with a PET scanner to estimate radiation attenuation correction for PET data.

In alternate embodiments of the invention, preliminary images of the patient can be obtained using a preliminary short PET scan, any external radioactive source, CT scanning devices, X-rays devices, MR, ultrasound devices, or any second imaging modality that is available.

In embodiments of the invention, random time coincidences are rejected by tailoring a time coincidence window to an a priori knowledge, using a complementary modality and the location of a patient—in the field of view of a PET scanner.

BRIEF DESCRIPTION OF THE DRAWINGS

The invention will now be more fully described by way of example with reference to the accompanying drawings in which.

DETAILED DESCRIPTION OF THE INVENTION

Figure 1:
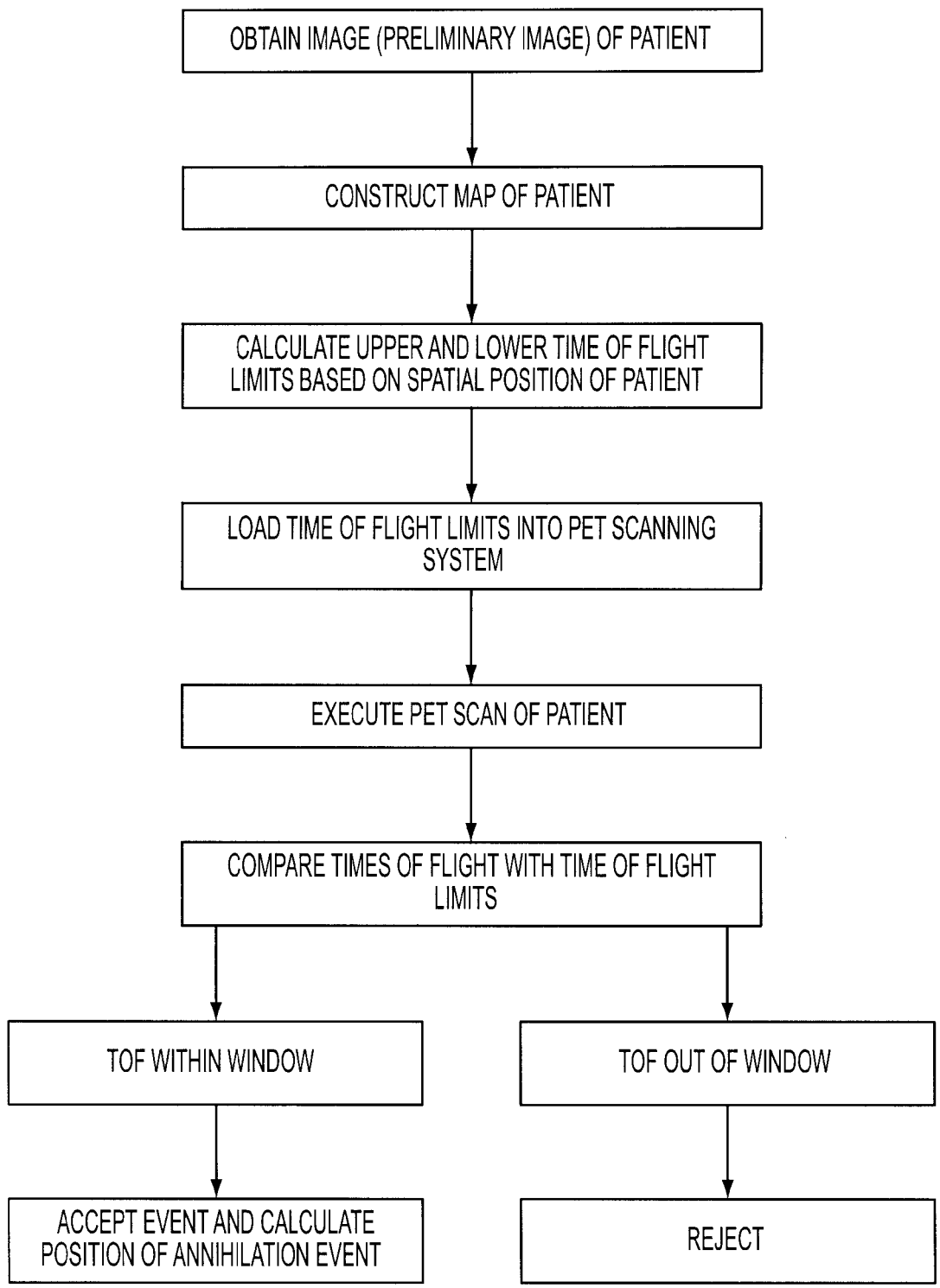
FIG. 1 is a flow diagram illustrating a method according to the present invention.

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention. As illustrated in FIG. 1, a method of acquiring PET images with a time coincidence window lower than the conventional limit generally comprises the steps of obtaining a preliminary image of a patient within the field of view of a PET scanning system, describing the spatial location of the patient within the field of view, computing a time coincidence window for each pair of oppositely disposed detectors based on the spatial location of the contour of patient and the probable intersection of such contour with the line connecting the detectors, scanning the patient with a PET scanning system to detect pairs of gamma photons produced by annihilation events, determining whether the detection of the pair of gamma photons occurs within the calculated time coincidence window, accepting and storing the event only if the detection of the gamma photons occurs within the time coincidence window, and processing the event in order to compute the location of the annihilation event and reconstruct the image of the original radioactivity distribution in the patient.

Most positron emission tomography (PET) devices include systems for measuring attenuation correction of emissions data, or are associated with secondary imaging modalities, e.g., PET/CT and PET/MR devices, etc. In one method according to the present invention, such attenuation correction system, or second imaging modality, is used to obtain independent measurements, or images, of a patient within a FOV. The images are then used to construct a map of the position of the patient within the FOV. More specifically, in an embodiment of the invention an external radiative source, such as Cs137, Ge68 or X-rays from a CT device, is used to construct an attenuation coefficient map, or $\mu$-map, of a patient that is to be scanned. The radiation emitted by the external radiative source is transmitted through the patient and the intensity of the radiation is measured by a plurality of detectors on an opposite side of the patient. The intensity information is then represented as a transmission sinogram.

Figure 2:
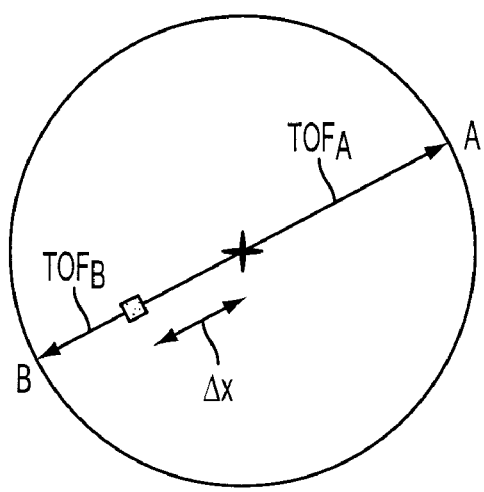
FIG. 2 is a schematic illustration of a Field-of-View (FOV) of a PET scanner wherein a radioactive source is disposed a distance $\Delta x$ from the center and A and B represent two generally oppositely disposed detectors.
Figure 3:
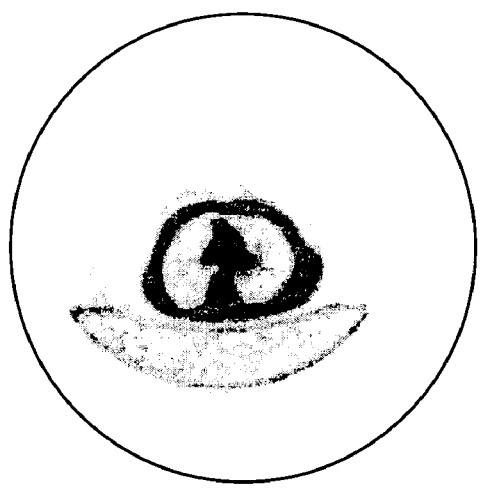
FIG. 3 is a transaxial view of an attenuation map ($\mu$-map) of a patient in the FOV of a PET scanner; in the figure, the patient is on a bed and the image plane is shown as passing through the patient's lung region.

As illustrated in FIG. 3, an attenuation coefficient map, $\mu$-map, of the patient in the FOV is prepared from a transmission sinogram. Typically, $\mu$-maps describe portions of a patient using a Cartesian coordinate system $\mu(x,y,z)$, wherein x, y and z describe planes or axial coordinates of the patient. The $\mu$-map of FIG. 2 illustrates a patient (and bed) inside a field of view of a PET scanning device and is a transaxial view of a plane passing through the lung portion of a patient.

Figure 4:
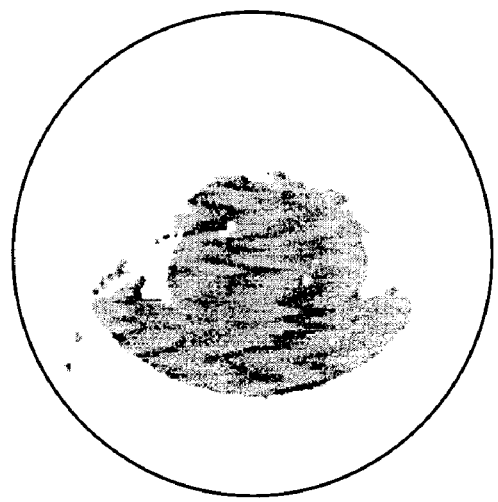
FIG. 4 is a binary image M(x,y,z) derived from the image of FIG. 3, which identifies probable positions in space occupied by a patient; and, FIG. 5 is a schematic illustration of a LOR identified by detectors A and B, the LOR intersects the binary image of FIG. 4 and identifies spatial limits for the TOF range ($\alpha$ and $\beta$).

As illustrated in FIG. 4, once $\mu(x,y,z)$ of the patient is known, a binary image of the patient and the space occupied by the patient within the FOV can be constructed. To create a binary image from the $\mu$-map, image pixels having $\mu(x,y,z)$, or attenuation coefficients, satisfying predetermined criteria are set to 1 and all remaining pixels are set to 0. The binary image, M(x,y,z), constructed therefrom is then used to identify all probable positions in space occupied by the patient.

Figure 5:
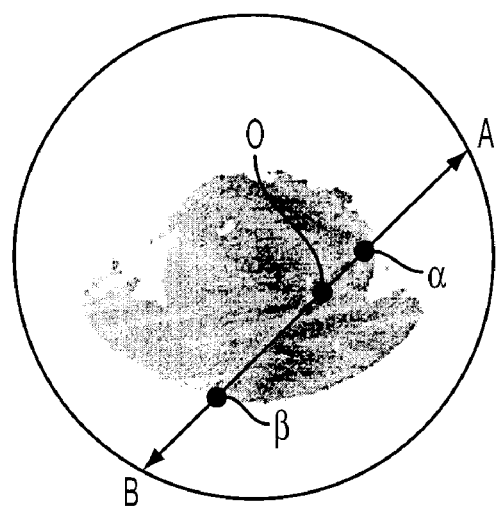

As illustrated in FIG. 5, because the purpose of the PET scan is to obtain an image of the localization of the source of radiation within the patient, the boundary or contour of the patient necessarily defines the spatial limit where annihilation events of interest occur. In view of this fact, one time coincidence window for each pair of detectors can be computed using the probable spatial location of the object described by the binary image and the line connecting the detector pair. As seen more clearly in FIG. 5, for each line of response (LOR) between a pair of oppositely -disposed detectors A and B, the intersection of a LOR with a profile of the patient image is identified and this information is then used to calculate corresponding upper and lower time of flight difference limits, $\tau_{low}$ and $\tau_{high}$, along the LOR. This information is then stored in a pair of arrays. More specifically, as illustrated in the figure, gamma photons propagating along $LOR_{AB}$ can be generated within the patient anywhere between point $\alpha$ and $\beta$, wherein $\alpha$ is the possible source of a pair of gamma photons closest to the detector A and $\beta$ is the possible source of a pair of gamma photons closest to the detector B. $\alpha$ and $\beta$ can be identified as the intersection points between the line segment connecting A and B and the contour or boundary of the patient. It is seen, then, that a pair of oppositely disposed gamma photons produced at $\alpha$ have a minimum possible time of flight difference while a pair of oppositely disposed gamma photons produced at $\beta$ have a maximum possible time of flight difference (because the distance from $\alpha$ to detector A is longer than the distance from $\beta$ to detector B, a gamma produced at, $\beta$ will take longer to reach detector A than a gamma produced at $\alpha$ will take to reach detector B, while a gamma produced at $\beta$ will reach detector B in a shorter time than a gamma produced at $\alpha$ will take to reach detector A). In other words, $(T_A-T_B)_\alpha = -2X_\alpha/c$ and $(T_A-T_B)_\beta = 2X_\beta/c$, where $X_\alpha$ and $X_\beta$ are the distances between the center of the segment connecting the two detectors and the points $\alpha$ and $\beta$ respectively, and $\alpha$ and $\beta$ are the intersections of the contour of the patient and the said segment. Consequently, for any time coincidence resulting from a pair of oppositely disposed gamma photons produced within the patient along a LOR, the time of flight difference of the gamma photons can be described by the equation: $-2X_\alpha/c < (T_A-T_B) < 2X_\beta/c$.

Generally, for a pair of detectors i and j in a PET scanning system, a $LOR_{ij}$ is identified and the distances $X_{ij\alpha}$ and $X_{ij\beta}$ computed based on the spatial location of the patient described by the binary image. The limits for time of flight range are then calculated and stored in two arrays: $\tau_{low}(i,j) = -2X_{ij\alpha}/c$ and $\tau_{high}(i,j) = 2X_{ij\beta}/c$. The lower and upper limits for TOF for each LOR are then loaded into the coincidence electronics of a PET scanning system. Thus, each detector pair is configured to define distinct time coincidence windows based on the a priori knowledge of the position of the patient along a LOR. Consequently, unlike known coincidence window algorithms in which events in detectors i and j are accepted if $|T_i-T_j|<\tau$, the present method allows detector and/or coincidence electronics to be programmed to accept time coincidences occurring between detectors i and j only where $\tau_{low}(i, j) < (T_i-T_j) < \tau_{high}(i, j)$. It should be appreciated that while points $\alpha$ and $\beta$ are points that intersect with a profile portion of the patient image, points $\alpha$ and $\beta$ can be selected to be proximate the intersection, for example, for accommodating movement of a patient that may occur after the spatial location of the patient within the FOV has been described. In an embodiment, the spatial position of the patient can also be determined at various time intervals during an image acquisition and adjusted accordingly.

Once the $\tau_{low}$ and $\tau_{high}$ arrays have been loaded into the electronics of the PET scanning system, a PET scan of the patient can be performed. When gamma photons are detected by the detectors their times of flight are compared with the $\tau_{low}$ and $\tau_{high}$ arrays to determine whether their times of flight fall within or outside of the time coincidence windows. For those gamma photons having TOFs falling within the time coincidence windows, the spatial location of the annihilation event producing those gamma photons is calculated and stored in a distribution of calculated annihilation event spatial locations representing the patient. Gamma photons having times of flight falling outside of the time coincidence windows are rejected.

Figure 6:
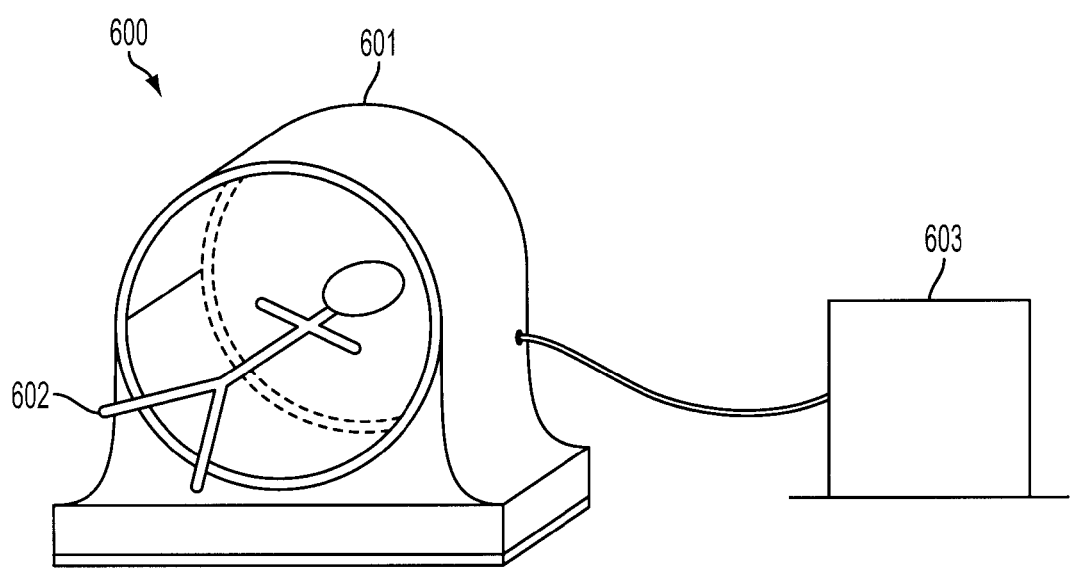
FIG. 6 is a perspective diagram of apparatus for acquiring PET images, in accordance with another aspect of the present invention.

FIG. 6 shows a PET imaging apparatus 600 for carrying out the novel image acquisition method of the present invention. As shown, the apparatus 600 includes a PET imaging device 601, and a processor 603 that is operatively coupled to the PET imaging device 601. A patient 602 is placed inside the imaging device 601 to be scanned, after a suitable radiopharmaceutical has been introduced into the body of the patient 602. The processor 603 is programmed to calculate time coincidence windows for each LOR based on an intersection of the LOR with a spatial location described by a preliminary image of the patient 602, and for each detected annihilation event, determines whether the detection of a gamma photon pair occurs within the time coincidence window corresponding to a LOR of the annihilation event. The processor 603 accepts data relative to the detection of the gamma photon pair only if the detection occurs within the calculated time coincidence window, and calculates a spatial location of the annihilation event for use in image reconstruction only if the event has been accepted.

It should be appreciated that while the exemplary embodiments of the invention described herein utilizes an external source of radiation (radioactive sources or CT) to construct attenuation coefficient maps ($\mu$-maps) and binary maps of the object within the FOV, the spatial position of the object within the FOV can be described utilizing other imaging devices capable of producing morphological images, e.g., any X-ray based device, magnetic resonance imaging devices, ultrasound devices, preliminary PET scan. For any such technique utilized, the pre-images generally need only to allow identification of the contour or boundary of the patient within the FOV.

Additionally, while the exemplary embodiment describes locations within the field of view using a Cartesian coordinate system, other coordinate systems may be utilized to define positions within the field of view, e.g. polar coordinate systems (r, $\theta$) can be used Also, depending upon the architecture of a PET scanning system, it may not be possible to set a TOF range for each pair of oppositely disposed detectors. Consequently, the present invention contemplates clusters of detectors having similar TOF ranges.

Also, non-ideal (non-zero) time resolution of existing PET scanning systems implies that the TOF limits can be blurred by the time resolution of the system. This is equivalent to convolve the profile of the patient along a LOR with the spatial equivalent of the time spread function, for example a Gaussian function with a FWHM (Full Width at Half Maximum) equal to the measured time resolution. Therefore, other embodiments of the invention can include blurring of $\tau_{low}$ and $\tau_{high}$, if such blurring is based on a time spread function depending on time resolution.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method of acquiring PET images of a patient comprising:
   obtaining a preliminary image of a patient;
   describing a spatial location of said patient using said preliminary image;
   for each line of response connecting a pair of oppositely disposed PET detectors, calculating a time coincidence window based on an intersection of said described spatial location with said line of response;

detecting a pair of gamma photons produced by an annihilation event;

determining whether the detection of said pair of gamma photons occurs within the calculated time coincidence window corresponding to a line of response of said annihilation event;

accepting data relative to the detection of said pair of gamma photons only if the detection of said gamma photons occurs within said time coincidence window;

calculating a spatial location of said annihilation event only if the annihilation event has been accepted; and, adding the calculated spatial location of said annihilation event to a stored distribution of calculated annihilation event spatial locations representing the radioactivity distribution in said patient.

2. The method of claim 1 wherein said preliminary image comprises a data representation of said patient.

3. The method of claim 2 wherein said preliminary image comprises a binary representation of said patient.

4. The method of claim 1 wherein said preliminary image comprises a visual representation of said patient.

5. The method of claim 4 wherein said preliminary image comprises a sinogram of said patient.

6. The method of claim 5 wherein an attenuation map is constructed from said sinogram.

7. The method of claim 6 wherein a binary representation of said preliminary image is constructed from said attenuation map.

8. The method of claim 1, further comprising the step of obtaining a preliminary image with an imaging device capable of producing a morphological image of said patient.

9. The method of claim 8 wherein said imaging device comprises one of a a computed tomography (CT), magnetic resonance (MR), ultrasound, X-ray scanning device, external radioactive source or preliminary PET scanning device.

10. The method of claim 1 wherein the spatial location of said patient is defined using a Cartesian coordinate system.

11. The method of claim 1 wherein the spatial location of said patient is defined using a polar coordinate system.

12. The method of claim 1 wherein for each said line of response, said time coincidence windows can be described by the equation:

$$\tau_{low}(i,j) < (T_i - T_j) < \tau_{high}(i,j);$$

wherein:

$(T_i - T_j)$ is the time of flight difference between the detection of a pair of gamma photons resulting from an annihilation event propagated along a line of response $LOR_{ij}$ between oppositely disposed detectors i and j;

$\tau_{low}(i,j) = -2X_{ij\alpha}/c$, is a lower limit for time of flight difference between detectors i and j;

$\tau_{high}(i,j) = 2X_{ij\beta}/c$, is an upper limit for time of flight difference between detectors i and j;

$X_{ij\alpha}$ is a distance from the center of the segment (placed along $LOR_{ij}$) connecting detector i and j and a point $\alpha$ along $LOR_{ij}$;

$X_{ij\beta}$ is a distance from the center of the segment (placed along $LOR_{ij}$) connecting detector i and j and a point $\beta$ along $LOR_{ij}$;

$\alpha$ and $\beta$ are points of intersection between $LOR_{ij}$ and the contour of the patient to be scanned; and, c is the speed of light.

13. Apparatus for acquiring PET images of a patient comprising:

an imaging device for obtaining a preliminary image of a patient;

a processor that (a) describes a spatial location of said patient using said preliminary image; (b) for each line of response connecting a pair of oppositely disposed PET detectors, calculates a time coincidence window based on an intersection of said described spatial location with said line; (c) for each detected pair of gamma photons produced by an annihilation event, determines whether the detection of said pair of gamma photons occurs within a calculated time coincidence window corresponding to a line of response of said annihilation event; (d) accepts data relative to the detection of said pair of gamma photons only if the detection of said gamma photons occurs within said time coincidence window; and (e) calculates a spatial location of said annihilation event for use in image reconstruction only if the event has been accepted.

14. Apparatus as claimed in claim 13, wherein said imaging device is selected from the group consisting of a a computed tomography (CT), magnetic resonance (MR), ultrasound, X-ray scanning device, external radioactive source or preliminary PET scanning device.

* * * * *